United States Patent
Decre et al.

(10) Patent No.: US 10,220,200 B2
(45) Date of Patent: Mar. 5, 2019

(54) DEVICE FOR CRANIAL IMPLANTATION, AND SYSTEM AND USE THEREOF

(75) Inventors: Michel Marcel Jose Decre, Eindhoven (NL); Johannes Cornelius Antonius Muller, Eindhoven (NL); Michel Gerardus Pardoel, Eindhoven (NL); Hubert Cecile Francois Martens, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 738 days.

(21) Appl. No.: 13/126,283

(22) PCT Filed: Nov. 3, 2009

(86) PCT No.: PCT/IB2009/054879
§ 371 (c)(1),
(2), (4) Date: Apr. 27, 2011

(87) PCT Pub. No.: WO2010/052642
PCT Pub. Date: May 14, 2010

(65) Prior Publication Data
US 2011/0213382 A1    Sep. 1, 2011

(30) Foreign Application Priority Data
Nov. 5, 2008   (EP) ..................... 08168340

(51) Int. Cl.
*A61N 1/05*  (2006.01)
*A61B 5/00*  (2006.01)

(52) U.S. Cl.
CPC .......... *A61N 1/0534* (2013.01); *A61B 5/6864* (2013.01); *A61N 1/0539* (2013.01)

(58) Field of Classification Search
CPC .. A61N 1/0534; A61N 1/0539; A61N 1/0529; A61B 19/00; A61B 5/6864
USPC .......... 606/129, 130; 600/378, 146; 607/116
See application file for complete search history.

(56) References Cited

U.S. PATENT DOCUMENTS

| | | | |
|---|---|---|---|
| 6,321,104 B1 * | 11/2001 | Gielen et al. | 600/378 |
| 6,324,433 B1 | 11/2001 | Errico | |
| 6,427,086 B1 | 7/2002 | Fischell et al. | |
| 7,346,391 B1 * | 3/2008 | Osorio et al. | 607/2 |
| 7,518,775 B2 * | 4/2009 | Miles et al. | 359/238 |
| 2001/0056290 A1 | 12/2001 | Fischell et al. | |
| 2005/0228249 A1 | 10/2005 | Boling | |
| 2006/0025704 A1 * | 2/2006 | Stendel et al. | 600/561 |
| 2007/0225773 A1 | 9/2007 | Shen | |
| 2007/0233158 A1 * | 10/2007 | Rodriguez | 606/130 |
| 2008/0140149 A1 * | 6/2008 | John | A61N 1/0529 607/45 |
| 2008/0172068 A1 * | 7/2008 | Adams et al. | 606/130 |

FOREIGN PATENT DOCUMENTS

EP    1016432 A2    7/2000

OTHER PUBLICATIONS

Office Action dated Feb. 8, 2014 for Chinese Patent Application No. 200980144160.

* cited by examiner

*Primary Examiner* — Diane Yabut
(74) *Attorney, Agent, or Firm* — Shumaker & Sieffert, P.A.

(57) ABSTRACT

A device for cranial implantation includes a ferrule and a plate for placement in the ferrule. Furthermore, a neurological implant system includes a probe and a device for cranial implantation.

17 Claims, 4 Drawing Sheets

DEVICE FOR CRANIAL IMPLANTATION, AND SYSTEM AND USE THEREOF

FIELD OF THE INVENTION

The present invention pertains to a device for cranial implantation. More specifically, the present invention pertains to a device for cranial implantation comprising a ferrule with a first hole.

BACKGROUND OF THE INVENTION

Within the field of neurotechnology, deep brain stimulation (DBS) is a surgical treatment involving the implantation of a medical device called a deep-brain stimulator, which sends electrical impulses to specific parts of the brain. DBS in certain brain regions has provided remarkable therapeutic benefits for otherwise treatment-resistant disorders such as chronic pain, Parkinson's disease, tremor and dystonia. Despite the long history of DBS, its underlying principles and mechanisms are still not clear. DBS directly changes brain activity in a controlled manner. Unlike lesioning techniques, its effects are reversible. Furthermore, DBS is one of only a few neurosurgical methods that allow blinded studies.

In principle, the deep brain stimulation system comprises two components: the implanted pulse generator (IPG), and the probe. The IPG is a battery-powered neuro stimulator that sends electrical pulses to the brain to interfere with neural activity at the target site. The IPG is typically encased in e.g. a titanium housing. The probe consists of about 10-40 cm long wires and a plurality of electrodes. The wires connect the IPG to the electrodes, which are located at the distal end of the probe. The IPG may be calibrated by a neurologist, nurse or trained technician to optimize symptom suppression and control side effects.

DBS probes are placed in the brain according to the type of symptoms to be addressed. All components are surgically implanted inside the body. The typical procedure is performed under local anaesthesia, where a hole is drilled in the skull and the electrode is inserted with feedback from the patient for optimal placement. The right side of the brain is stimulated to address symptoms on the left side of the body and vice versa.

Commercially available DBS systems consist of a chest-implanted IPG, a connector cable of approximately 30 cm running subcutaneously from the IPG to the top of the patient's head, and a lead cable connected proximally to the connector cable by means of a connector, which may be approximately 20 mm long and 4-5 mm in diameter. The lead cable carries 4 electrodes distally, and is itself rather long, around 30 cm, so that a lot of excess length has to be left under the patient's scalp. This system has several disadvantages:

the fixation of the lead cable is difficult and it is liable to lead displacement and inaccuracies;
the long cables cause irritation and erosion of the skin;
the cables are the source of lead break;
infection can propagate subcutaneously along the cable into the brain; and
the long and uncontrolled cable bundles give rise to potentially dangerous voltages when submitted to the electromagnetic fields of a Magnetic Resonance Imaging scanner (MRI).

US 2005/0,228,249 proposes solutions to the afore-mentioned by providing an IPG mounted in a ferrule, intracranially after a craniotomy is performed in the parietal bone, with the IPG device mounted into the ferrule, and further connected to seed electrodes by means of a seed electrode interface that can have the shape of a burrhole cover, or be simply a subcutaneous module.

However, this solution still needs cables running subcutaneously, to cranial positions, possibly quite remote from the parietal position of the ferrule-mounted IPG. This may give rise to unwanted motion of the wire, which lead to mechanical forces on the probe and thus potential damage to brain tissue. Also, the probe wire must have extra length to allow manipulation of the implantable device before the implantation. When this excess wire is stored subcutaneously after placement of the probe, it may lead to irritation, skin erosion, and potentially infection.

Hence, an improved way of mounting a DBS probe, allowing for increased flexibility, cost-effectiveness, safety and user friendliness would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least one of the above mentioned problems e.g. by providing a cranial implant device.

In an aspect, a device for cranial implantation allowing for adjustment of positioning of a probe is provided. The device comprises a ferrule forming a first hole there through. The device also comprises a plate for placement in the ferrule. The plate is provided with a second hole, such that when the plate is placed in the ferrule, the first hole and the second hole at least partly coincides enabling accommodation of the probe. This provides for the advantage that the probe does not have to be placed in the middle of the first hole, but instead the positioning of the probe is adaptable, which is especially useful since the surgeon usually does not know exactly where the probe is to be placed prior to the surgery. The device provides for increased flexibility, cost-effectiveness, safety and user friendliness. Moreover, in use the device provides for less discomfort for the patient.

In an aspect, a neurological implant system is provided. The system comprises a probe and the device for cranial implantation is disclosed providing for less risk of potentially infection.

In another aspect, use of the device for cranial implantation for adjustment of positioning of a deep brain stimulation probe is provided.

Other embodiments and advantages will be disclosed in the following.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION FO DETAILED EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Figure 1:
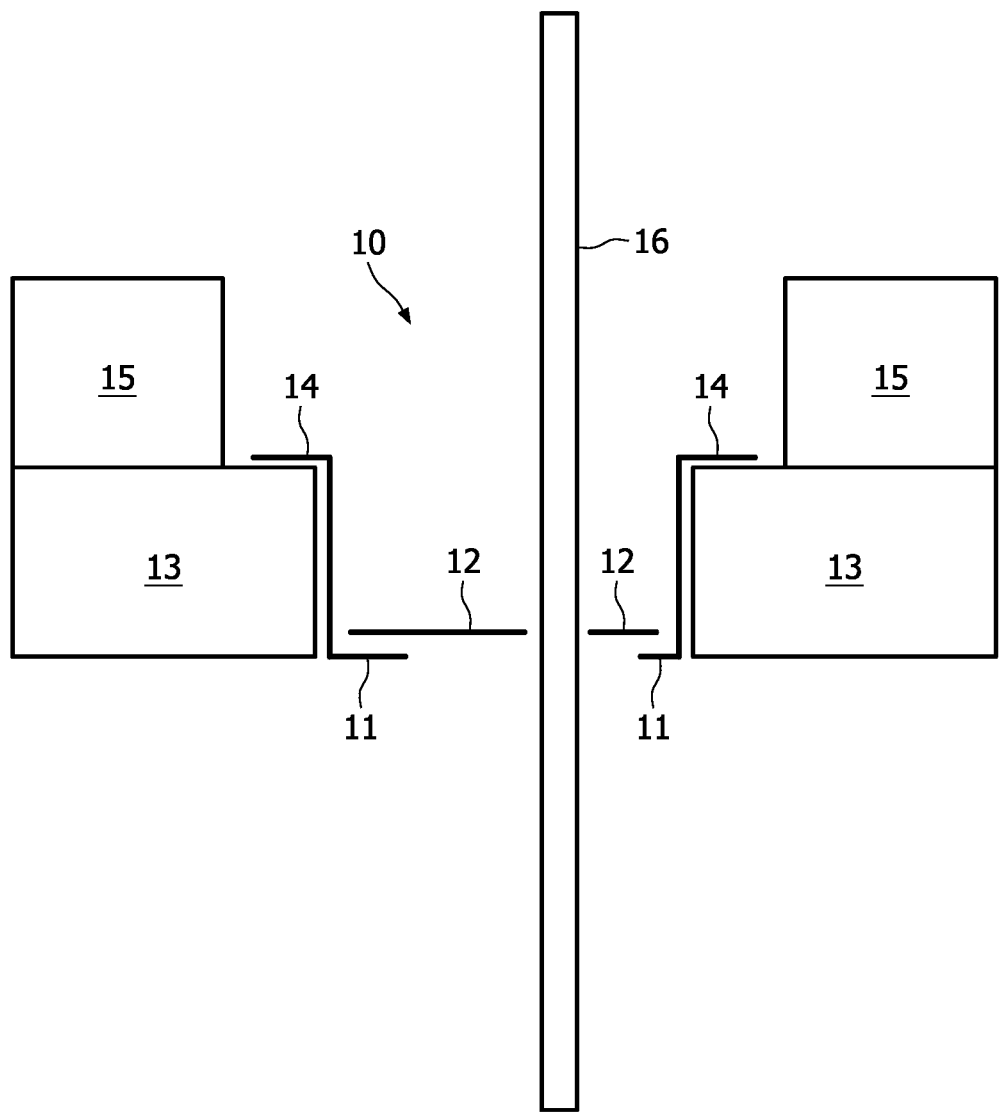
FIG. 1 is a sectional view of a device according to an embodiment.

In an embodiment according to FIG. 1, a device 10 for cranial implantation is provided. The device 10 for cranial implantation is allowing for adjustment of positioning of a probe 16 comprises a ferrule 11, forming a hole there through, and a plate 12 for placement in the ferrule. The plate 12 is being provided with a hole, such that when the plate 12 is placed in the ferrule 11, the hole of the ferrule and the hole of the plate at least partly coincides enabling accommodation of the probe 16.

In use the ferrule 11 is positioned in a hole provided in the cranium 13 of a patient. The hole of the ferrule 11 is provided such that it faces towards the brain. The hole provided through the ferrule may have a cylindrical shape. The ferrule 11 has an edge 14, in use being located on the side facing away from the brain. The edge 14 is positioned to be in contact with the cranium 13 to stop the ferrule from moving towards the brain. The plate 12 has a hole positioned in such a way that the hole of the ferrule and the hole of the plate at least partly coincides enabling accommodation of the probe 16. In this way, a path enabled by the hole of the ferrule and the hole of the plate is created, through which a probe 16 may be inserted in the brain through the ferrule 11 and the plate 12.

In one embodiment, the plate 12 is configured with an outer structure enabling rotable placement in the ferrule 11. In this embodiment, the ferrule 11 has an inverted, or corresponding, structure for receiving the outer structure of the plate 12. The outer structure of the plate 12 may e.g. comprise protrusions 23, such as cogs, which may be received by a corresponding structure 24 of the ferrule 11. When the hole is non-concentrically provided in the plate 12, by rotating of the plate 12 in relation to the ferrule 11, the position of the plate hole will change in relation to the ferrule 11. Accordingly, the position of the path being rendered by the coinciding plate hole and ferrule hole will also change by rotation of the plate 12 in relation to the ferrule 11.

Figure 2:
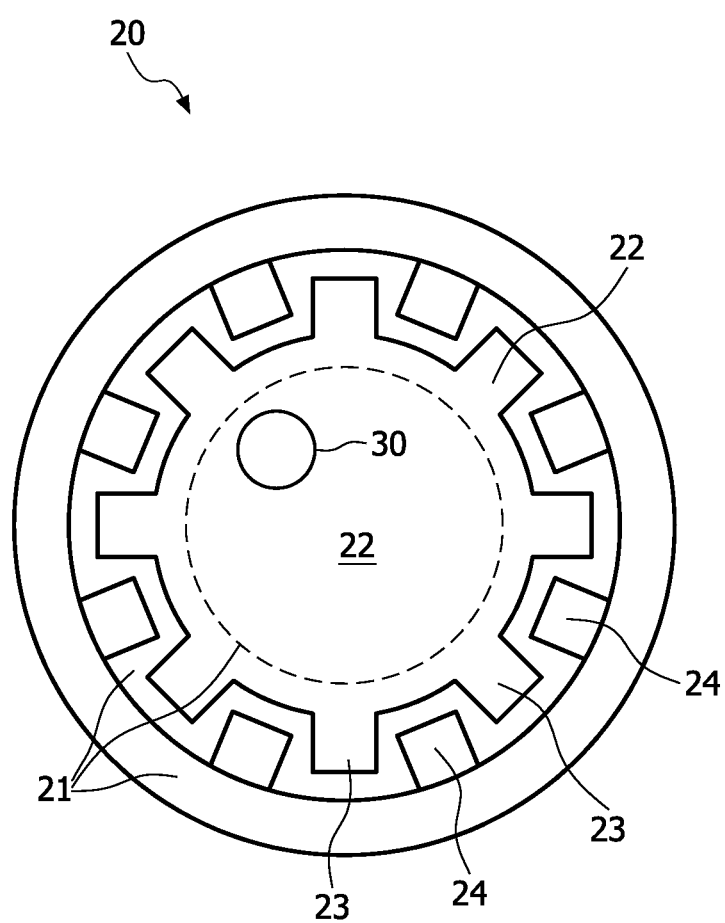
FIG. 2 is a top view of a device according to an embodiment.

In an embodiment, according to FIG. 2, a device 20 for cranial implantation is provided, wherein after placement of the plate 22 in the ferrule 21, due to the configuration of the structure of the plate 22, in FIG. 2 shown as cogs, further rotation of the plate 22 in relation to the ferrule 21 will be prevented. In FIG. 2 the plate is placed above the ferrule. The hole of the ferrule is indicated as a dashed line, indicating that the ferrule hole is located beneath the plate. An advantage with this is that the plate 22, and thus the position of the probe, by means of the hole 30 provided in the plate, is stabilized when the plate 22 has been positioned in the ferrule 21. This means that the probe will be prevented from sliding in use. However, adjustment of the position of the probe may still be possible by lifting the plate 22 from the ferrule 21, and rotate the plate in relation to the ferrule, in order to change the position of the hole 30.

In another embodiment, the plate 12 is configured with an outer structure enabling rotation in relation to the ferrule 11 while placed in the ferrule 11. In this embodiment the outer structure of the plate 12 may be a smooth surface, e.g. enabling a mutual sliding motion against the ferrule 11.

An advantage rendered by the above-mentioned embodiments is that the probe does not have to be placed in the middle of the hole of the ferrule 11, since the positioning of the probe is determined by the placement of the hole of the plate 12, the plate's rotation in relation to the ferrule 11, and/or the location at which the hole of the ferrule 11 and the hole of the plate 12 coincides. This is especially useful since the surgeon usually does not know exactly where the probe is to be placed from the beginning of the surgery. In this way the positioning of the path enabling insertion of the probe is made adaptable.

The ferrule 11 may be mounted in the hole in the cranium 13 and fixed to the cranium 13 with methods well known to a person skilled in the art, such as glue, bio cement or thread.

After the ferrule 11 has been placed in the cranium, the brain is still accessible and visible to the physician. The plate 12 is then positioned over the probe 16. The probe 16 may then be placed in the brain after an extra electro-physiological analysis of the target tissue. After the probe 16 has been correctly positioned in the brain, the probe 16 is mechanically fixated by positioning the plate 12 so that it may be fixated to the ferrule, e.g. by glue. The ferrule is thus completely closed.

Figure 3A:
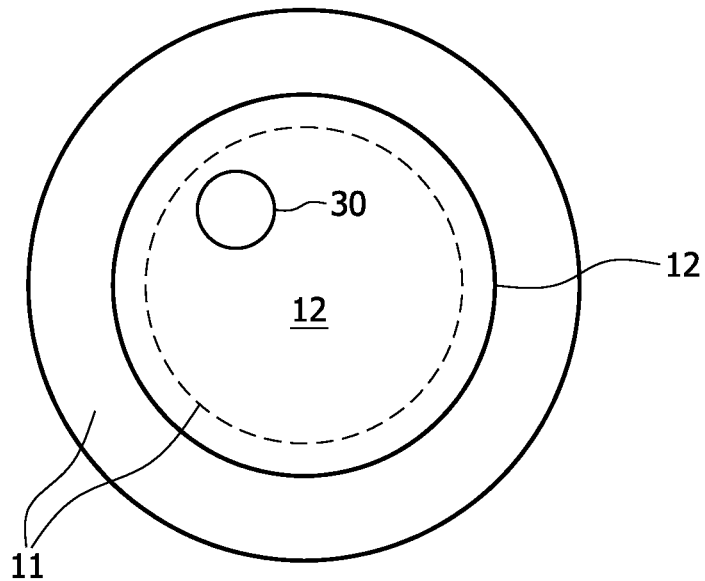
FIG. 3A is a bottom view of the device according to an embodiment.

In FIG. 3, the positioning of the plate according to an embodiment is visualized. FIG. 3A is showing the ferrule 11 from inside the cranium. The second hole 30 in the plate 12 may be positioned anywhere in the plate 12, if it is placed on a suitable distance from the centre of the plate 12. The ferrule 11 may thus have a circular shape with a concentric circular first hole. The plate 12 may have a circular shape with an eccentric circular hole. If slided and turned correctly, the plate 12 will then always cover the first hole in the ferrule 11. However, the plate 12 may also be placed eccentric with respect to the ferrule 11.

However, the shape of the ferrule 11, plate 12, the first hole and the second hole 30 may be in any form such as elliptic, rectangular, triangular etc.

In an embodiment, the first hole in the plate 12 is a slot. This increases flexibility, since the probe location may be moved along the length of the slot and thereby adjusted. The slot space, which is not occupied by the probe, may then be closed with glue or bio cement.

The suitable distance may be calculated with the following formulas:

$$D3+D4+2*E=2*D2+1$$

$$D3-2*E=D2+1$$

$$D1-D2-D3+D4+2*E=0$$

Wherein D1 is the inner diameter of the ferrule, D2 is the diameter of the first hole, D3 is the diameter of the plate 12 and D4 is the diameter of the hole 30 in the plate 12. E is the eccentricity, or the distance between the centre of the plate to the centre of the hole 30 in the plate 12.

In an embodiment, where the outer diameter of the ferrule is 20 mm, D1 is 19.2 mm, D2 is 9.7 mm, D3 is 15 mm, and D4 is 1.27 mm, E will be 2.1 mm.

Figure 3B:
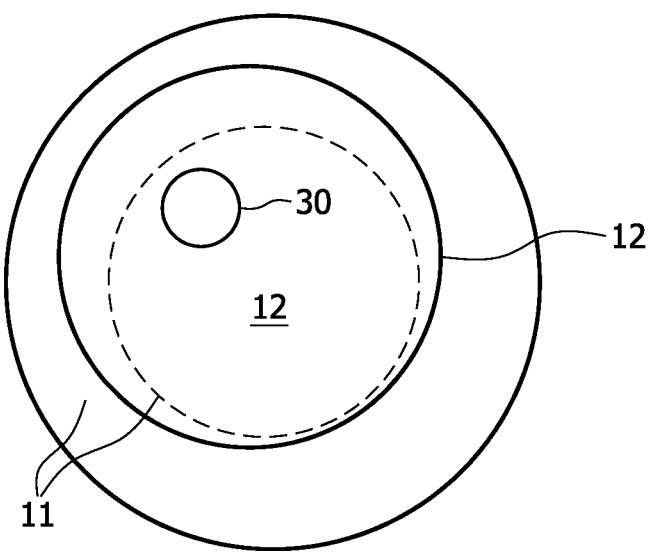
FIG. 3B is a top view of a device according to an embodiment.

FIG. 3B is showing the ferrule 11 from outside the cranium. After the plate 12 has been fixated to the ferrule 11, the probe 16 may also be fixated to the plate, e.g. with glue.

Figure 4:
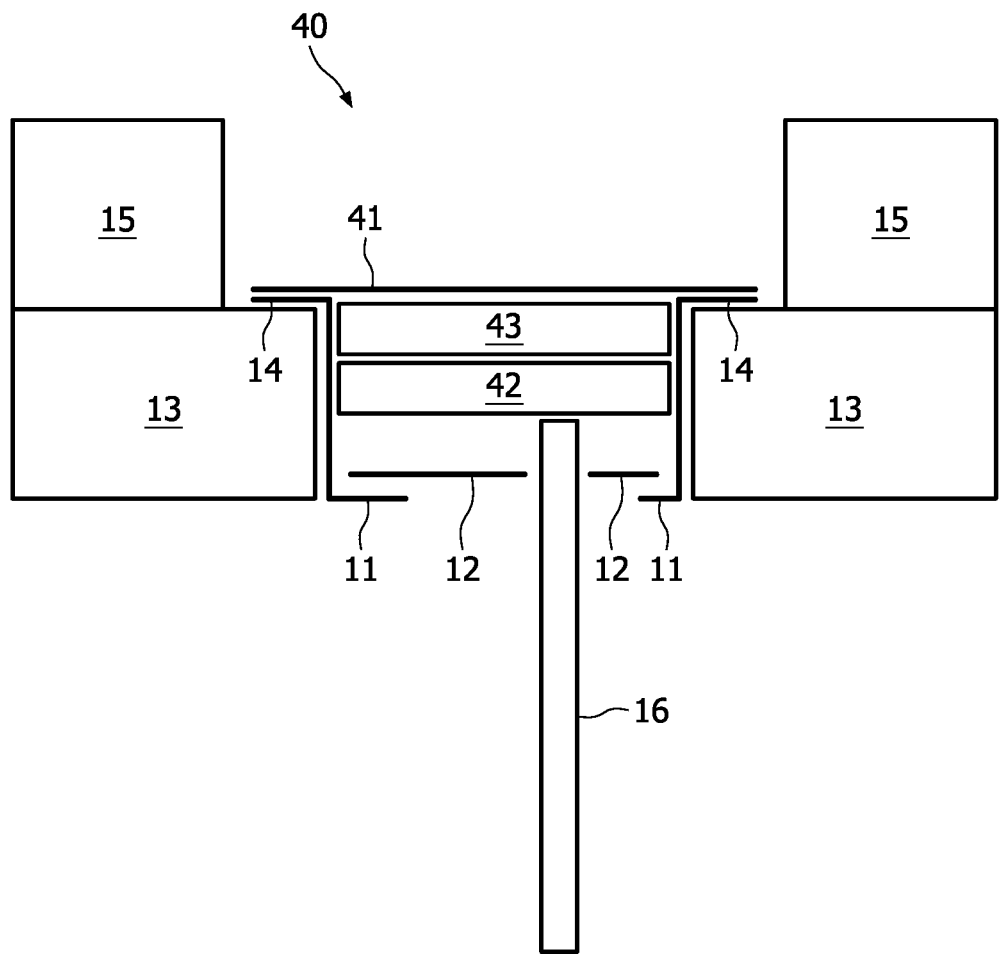
FIG. 4 is a sectional view of a device according to an embodiment.

In an embodiment according to FIG. 4, a device for cranial implantation 40 is provided. The device allowing for adjustment of positioning of a probe 16 comprises a ferrule 11, forming a first hole there through, and a plate 12 for placement in the ferrule. The plate 12 is being provided with a second hole, such that when the plate 12 is placed in the ferrule 11, the first hole and the second hole at least partly coincides enabling accommodation of the probe 16. Furthermore, the device for cranial implantation 40 comprises a lid 41 for fixing the lid 41 to the ferrule 11, thus closing the ferrule, e.g. by glue or bio cement. When the device for cranial implantation 40 is closed with the lid 41, the scalp 15 may be closed. In an embodiment, the device for cranial implantation 40 comprises electronics 42 and a power source 43, such as a battery, for driving the electronics 42. The electronics 42 may be connected to the probe 16. The probe 16 may be curled up inside the ferrule 11 so that the excess probe length may be stored in the ferrule 11. Since the curling of the excess length takes place after the plate 12 has fixated the probe 16, the brain is already protected from these mechanical actions.

In an embodiment, the electronics comprised in the device for cranial implantation comprises a battery, a pulse generator, a multiplexer, a board such as a printed circuit board or a flexible board, and a connector. However, the electronics may be any kind of electronics for regulating the probe, known to a person skilled in the art. Since the probe 16, electronics 42 and power source 43 is collected in the ferrule 11 and sealed on one side, towards the brain, with the plate 12 and on the other side, towards the scalp 15, with the lid 41, the device for cranial implantation 40 is safer from infection compared to prior art methods. Furthermore, the risk of displacement of parts is lower, as well as the risk of wear and tear.

In an embodiment, the ferrule 11, the lid 41 and the plate 12 are made of titanium. However, other materials may be possible, as will be appreciated by a person skilled in the art.

In an embodiment, a neurological implant system comprising a probe 16 and a device 10 for cranial implantation is provided.

In an embodiment, use of the device 10 for cranial implantation for adjustment of positioning of a deep brain stimulation probe is provided.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A device for cranial implantation allowing for adjustment of positioning of a probe, the device comprising:
a ferrule defining an inner surface, the inner surface forming a first hole through the ferrule;
electronics and a power source disposed within the first hole of the ferrule formed by the inner surface;
a lid configured to close the ferrule towards a scalp; and
a plate configured to be placed in the ferrule, the plate defining a second hole configured to accommodate the probe, wherein the first hole and the second hole at least partly coincide enabling accommodation of the probe at least partially within the first hole and the second hole when the plate is placed in the ferrule, wherein the plate is configured with an outer structure comprising protrusions, and wherein the ferrule is configured with a structure that receives the outer structure of the plate, such that receiving the outer structure of the plate by the structure of the ferrule prevents the plate from rotating in relation to the ferrule when the plate is placed in the ferrule.

2. The device according to claim 1, wherein the second hole is circular.

3. The device according to claim 1, wherein the second hole is a slot.

4. The device according to claim 1, wherein the ferrule is configured to be fixed to a cranium.

5. The device according to claim 1, wherein the lid is configured to be fixed to the ferrule.

6. The device according to claim 1, wherein the ferrule, the plate, and the lid are all made of titanium.

7. The device according to claim 1, wherein the ferrule includes a hollow cylinder.

8. The device according to claim 1, wherein the ferrule includes an outwardly extending upper flange.

9. The device according to claim 1, wherein the ferrule includes an inwardly extending lower flange configured to engage the plate.

10. The device according to claim 1, wherein the second hole is smaller than the first hole, the second hole having a second center unaligned with a first center of the first hole.

11. The device according to claim 1, wherein the lid is configured to be generally flush with a cranium.

12. The device according to claim 1, wherein a second diameter of the second hole is approximately equal to a first diameter of the probe.

13. The device according to claim 1, wherein the positioning of the probe is adjusted by rotation of the plate in relation to the ferrule.

14. The device according to claim 1, wherein the positioning of the probe is adjusted by changing a position of the second hole with respect to the ferrule.

15. The device according to claim 1, wherein the second hole has a second diameter smaller than a first diameter of the first hole and is configured to move relative to the first hole.

16. A neurological implant system comprising:
a probe; and
a device configured for cranial implantation and adjustment of positioning of the probe, wherein the device comprises;
a ferrule defining an inner surface, the inner surface forming a first hole through the ferrule;
electronics and a power source disposed within the first hole of the ferrule formed by the inner surface;
a lid configured to close the ferrule towards a scalp; and
a plate configured to be placed in the ferrule, the plate defining a second hole configured to accommodate the probe, wherein the first hole and the second hole at least partly coincide enabling accommodation of the probe at least partially within the first hole and the second hole when the plate is placed in the ferrule, wherein the plate is configured with an outer structure comprising protrusions, and wherein the ferrule is configured with a structure that receives the outer structure of the plate, such that receiving the outer structure of the plate by the structure of the ferrule prevents the plate from rotating in relation to the ferrule when the plate is placed in the ferrule.

17. The neurological implant system according to claim 16, wherein the probe is configured as a deep brain stimulation probe.

\* \* \* \* \*